United States Patent [19]

Kalb et al.

[11] Patent Number: 5,007,897

[45] Date of Patent: Apr. 16, 1991

[54] DRUG DELIVERY CATHETER

[76] Inventors: Irvin M. Kalb, 327 Alta Ave., Santa Monica, Calif. 90402; Michael J. Ram, 1 Horseshoe Rd., Bell Canyon, Calif. 91307

[21] Appl. No.: 358,083

[22] Filed: May 30, 1989

[51] Int. Cl.⁵ ............................................. A61M 25/00
[52] U.S. Cl. ...................................... 604/43; 604/96; 604/265
[58] Field of Search ........................ 604/840.1–892.1, 604/27, 41, 43, 45, 246, 265, 93, 94, 96, 104, 284, 285, 286, 280, 278; 606/192, 193; 600/29–31; 128/DIG. 25, 918

[56] References Cited

U.S. PATENT DOCUMENTS

| | | | |
|---|---|---|---|
| 3,394,705 | 7/1968 | Abramson | 604/280 |
| 3,593,713 | 7/1971 | Bogoff | 604/96 |
| 3,598,127 | 8/1971 | Wepsic | 604/265 |
| 3,699,956 | 10/1972 | Kitrilakis et al. | 604/265 |
| 3,815,608 | 6/1974 | Spinosa et al. | 604/105 |
| 3,977,408 | 8/1976 | Mackew | 604/102 |
| 3,981,299 | 9/1976 | Murray | 604/43 |
| 4,062,363 | 12/1971 | Bonner Jr. | 604/54 |
| 4,186,745 | 2/1980 | Lewis et al. | 604/265 |
| 4,417,576 | 11/1983 | Baran | 604/101 |
| 4,553,959 | 11/1985 | Hickey et al. | 604/96 |
| 4,623,329 | 11/1986 | Drobish et al. | 604/265 |
| 4,710,168 | 12/1987 | Christopher | 128/DIG. 25 |

FOREIGN PATENT DOCUMENTS

| | | | |
|---|---|---|---|
| 3441586 | 5/1986 | Fed. Rep. of Germany | 604/96 |
| 1280481 | 11/1961 | France | 604/101 |
| 8903232 | 4/1989 | PCT Int'l Appl. | 604/890.1 |
| 0674134 | 6/1952 | United Kingdom | 604/96 |

Primary Examiner—John D. Yasko
Assistant Examiner—Anthony Gutowski
Attorney, Agent, or Firm—Michael J. Ram

[57] ABSTRACT

The invention comprises a system for the long term continuous delivery of medication to hollow body organs. It is particularly suited for the deivery of chemotherapy drugs to lesions in the walls of those organs. The invention, specially designed for the treatment of the prostate gland, comprises a urinary drainage catheter which has an additional lumen within the wall thereof, said lumen proximate end connected to a space external of the catheter wall enclosed by a porous membrane. The distal end of the lumen, which is external to the penis when the catheter is positioned in the body, has a valved end for introduction of liquid medication therethrough. In use, the catheter is placed within the urethra, with the porous membrane portion adjacent the prostatic ducts. Medication introduced through said valve is transmitted along the lumen into the space between the catheter and the porous membrane, through the membrane and into contact with the prostatic ducts.

4 Claims, 4 Drawing Sheets

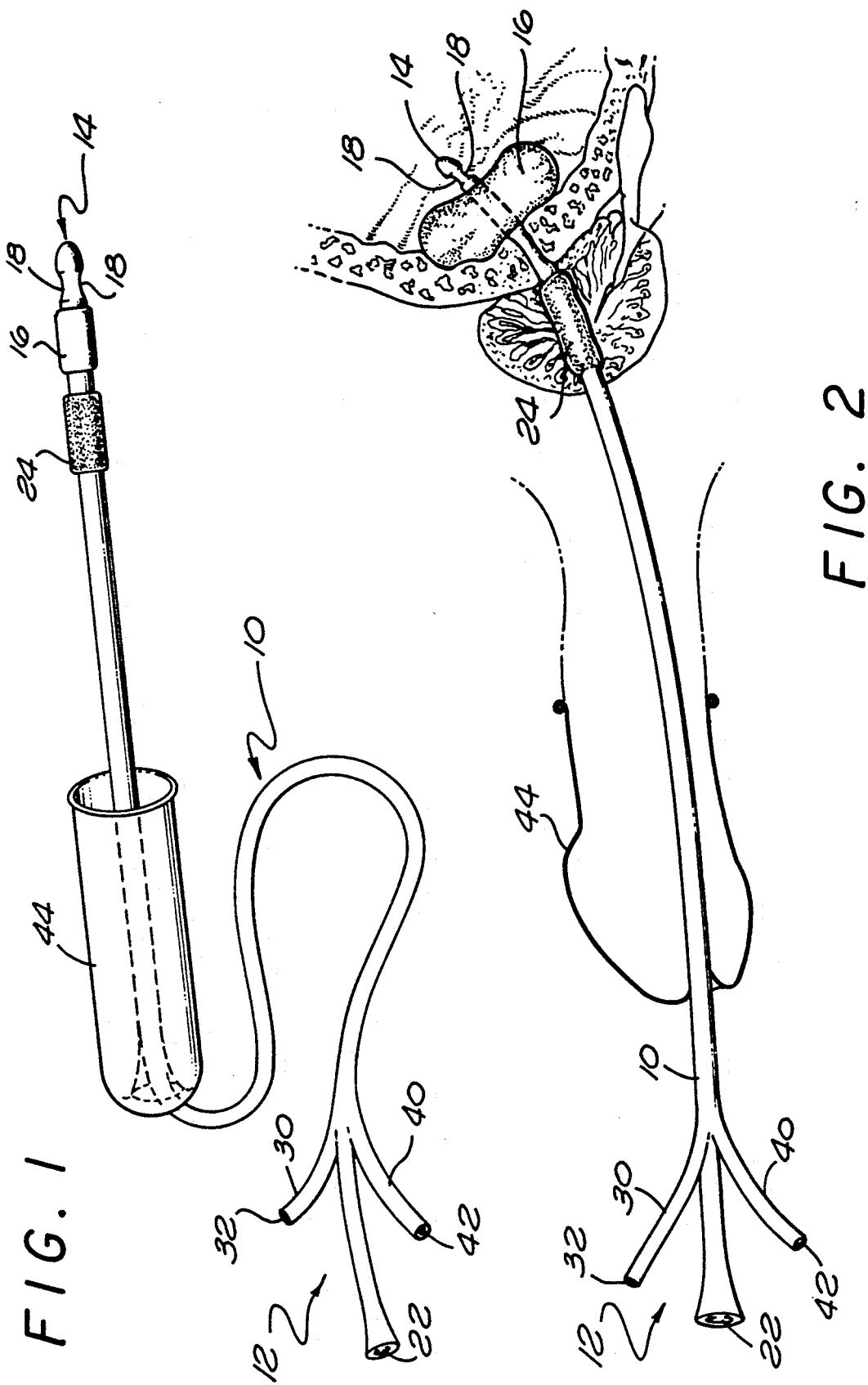

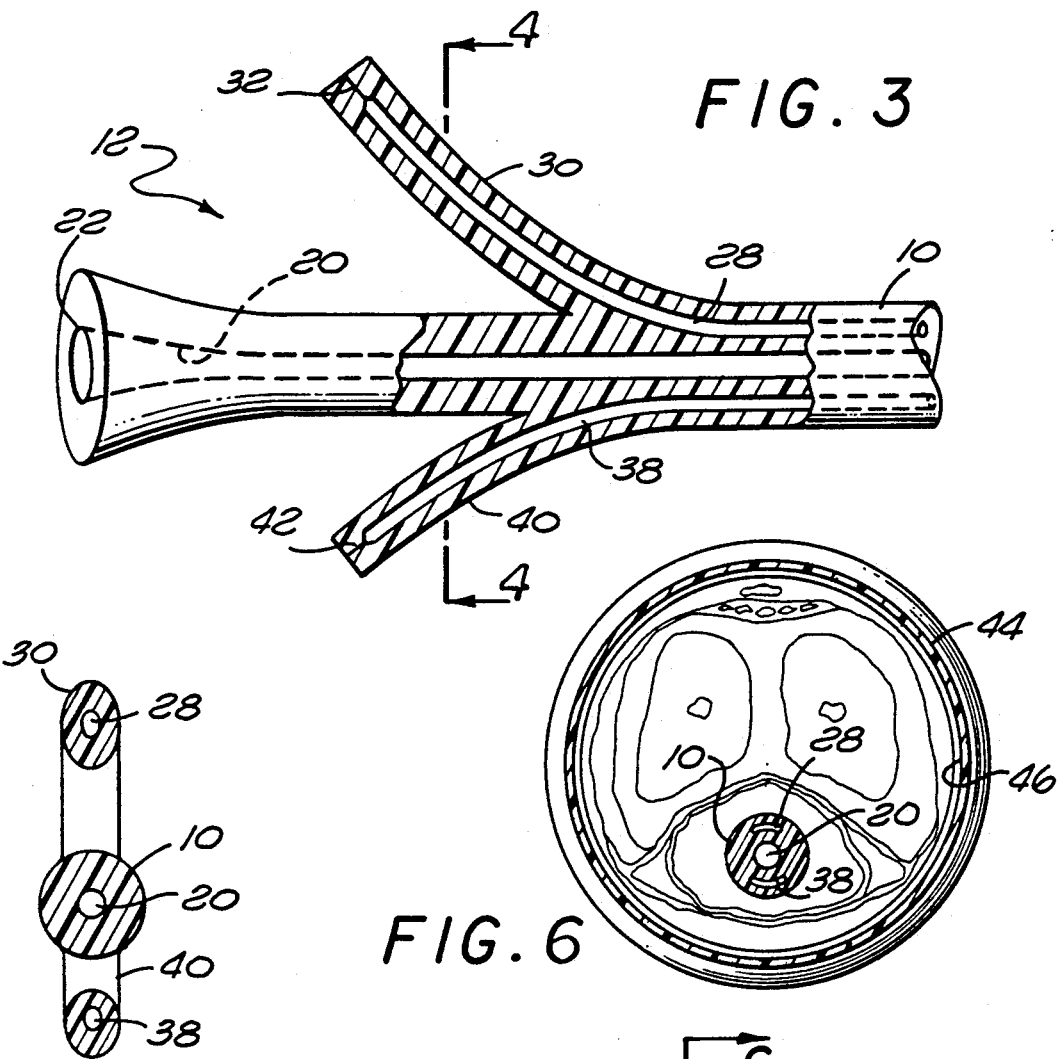
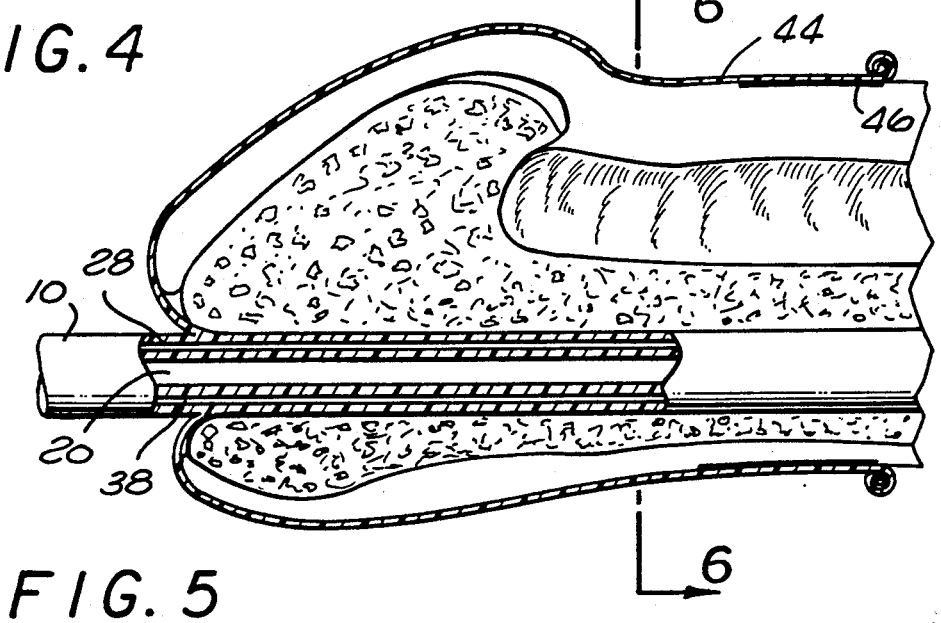

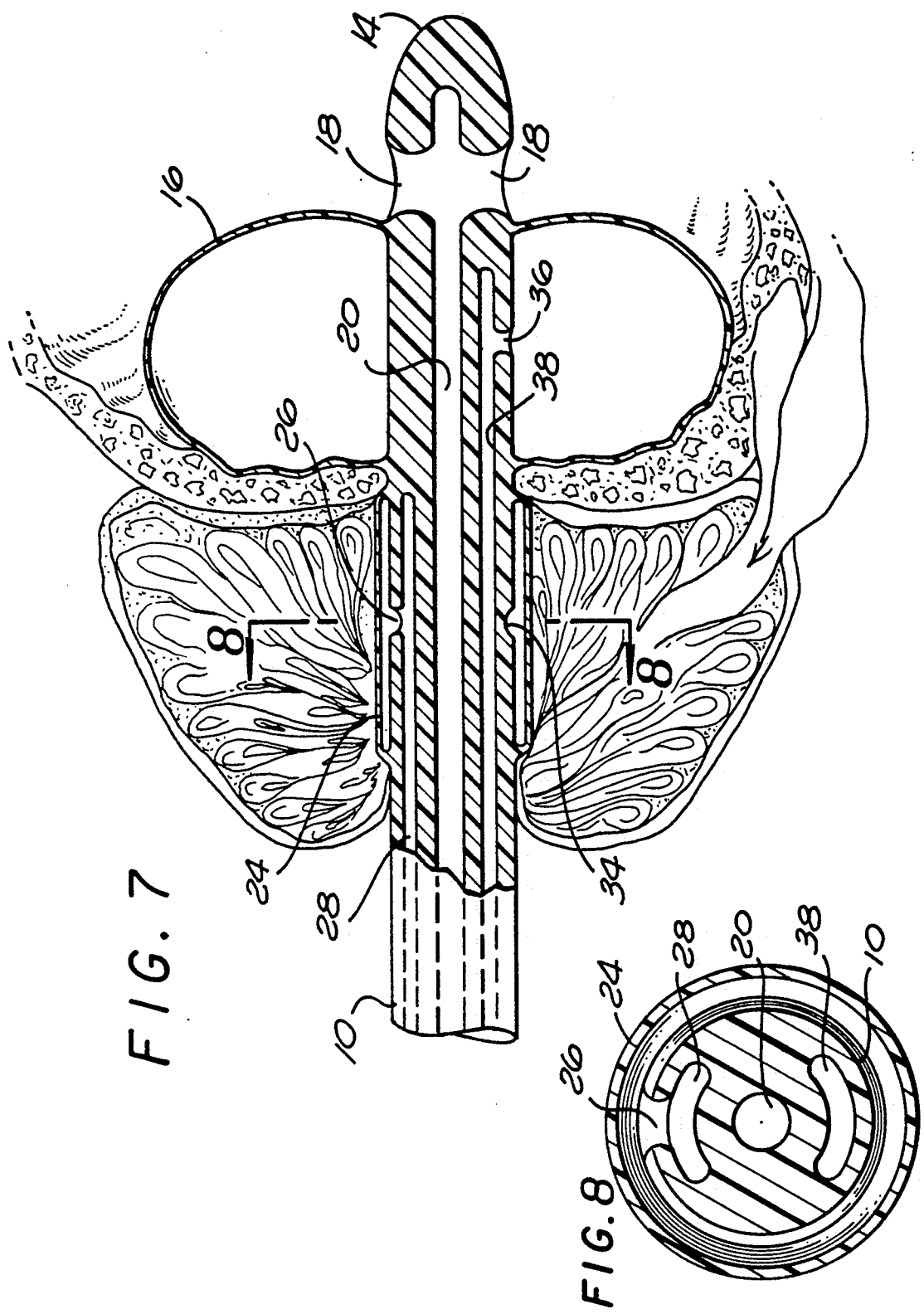

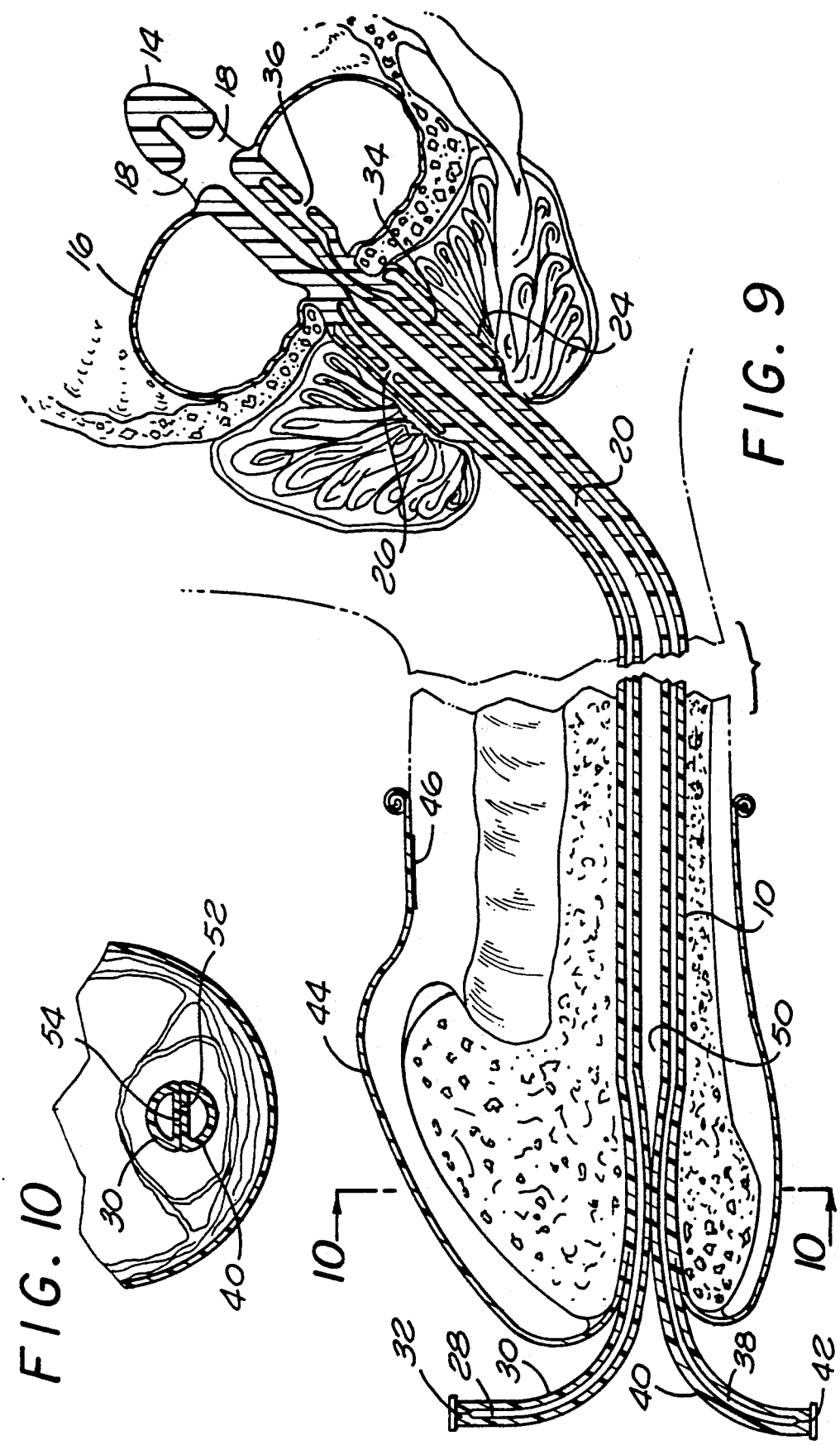

DRUG DELIVERY CATHETER

BACKGROUND OF THE INVENTION

This invention generally relates to a device for delivering drugs to hollow body organs such as the urinary system, the female reproductive system, the anal tract, or the ear, nose or throat. In particular, the invention is specially suited for treatment of the prostate gland.

The term "drug" as used herein is used in its broadest sense and can be diagnostic agents such as radiopaque visualizing agents for use in x-ray or fluoroscopic techniques or may be antibiotic, chemotherapy or other materials used to treat the body.

For example, disfunction or diseases of the prostate gland, an organ within the male urinary system, can be treated by systemic delivery of therapeutic agents. However, these agents must be delivered in high doses when given systemicly or they will not be effectively delivered to the prostate. In addition, these therapeutic agents can be very toxic to the body as a whole causing unwanted side effects. The preferred procedure is to deliver the drug directly to the prostate gland. This is difficult because of the small size of the prostate and the inaccessible location of the gland. The best procedure is to introduce the drugs into the prostate ducts which are accessible through the urethra at a point close to its entry into the bladder.

Several devices have been proposed for delivery of drugs to body organs. Devices for accessing the prostatic ducts all have deficiencies which limit their applicability. Latex, silicone or other polymer based catheters of the Foley design have been proposed for delivering the drugs. One proposal is to place grooves or channels on the outer surface of the catheter so that fluids used to irrigate the bladder can be allowed to wash the outer surface of the catheter and the wall of the urethra. This defeats the purpose of the Foley catheter as it allows leakage of urine from the bladder and establishes a path for retrograde infection. Merrill, U.S. Pat. No. 4,055,682, has disclosed techniques for coating a silicone catheter with a hydrophilic polymer such as N-vinyl pyrrolidone, hydroxy ethyl methacrylate or combinations thereof. Gould discloses in U.S. Pat. No. 4,156,067 the application of hydrophilic polyurethane polymers to the surface of catheters. The hydrophilic coatings on these catheters can be used as carriers for the delivery of water soluble drugs. These drugs are blended into the coatings before they are applied to the catheter or the region of the catheter which would be placed adjacent to the prostatic ducts can be dipped into the desired therapeutic agent before the catheter is placed in the urethra. However, there is a problem controlling the rate of delivery of the drug and the dosage level with such a device and the catheter must be removed and replaced periodically if the drug is to be replenished. Every time a catheter is removed and replaced the chance of introducing infectious agents increases.

U.S. Pat. No. 3,977,408 issued to MacKew discloses a Foley catheter with an extra conduit the proximal end of which exits through the wall of the catheter at a point which is positioned adjacent the area of the prostate when the catheter is positioned in the urethra. This allows the delivery of medication directly to a single point along the urethra. There is no way of controlling the exact point for delivery of drugs, to assure that the drug is dispersed around the full 360° of the urethra, or to reliably restrict the drug delivered from disbursing along the length of the urethra and leaking out of the penis. It is suggested that a clamp on the penis be used but this is uncomfortable to the patient and would crush the delivery and drainage lumen preventing delivery of the drug and drainage of urine from the bladder. This is a major deficiency as it may be necessary for certain drugs, such as chemotherapy agents, to be delivered continuously over a period of days, weeks, or even months.

While the prior art has attempted to address the problem of delivering drugs to the prostate gland, the prior art devices do not address all the problems, are inefficient, cause new problems, and do not allow a controlled continuous delivery of drugs.

SUMMARY OF THE INVENTION

The present invention consists of a tube with means for the delivery of a medication to a porous walled bladder designed to be positioned against the wall of the internal body organ being treated. It is particularly usefully for treating cancerous lesions of hollow body organs.

A particular embodiment of the present invention consists of a urinary drainage catheter with a retention means for placement in the bladder, an expandable sack with a drug permeable membrane wall surrounding the catheter in the region of the prostate gland, a drug delivery lumen in the wall of the catheter connecting the distal end of the catheter with the drug permeable sack, and a condom like sheath for placement over the meatus of the penis to prevent the catheter from sliding up the urethra into the bladder.

BRIEF DESCRIPTION OF THE DRAWINGS

FIG. 1 is a perspective view illustrating the invention in the form of a urinary catheter.

FIG. 2 is a perspective view showing an embodiment of the invention placed in the urinary tract for delivery of medication to the prostate.

FIG. 3 is an enlarged view partially in section of the distal end of the catheter.

FIG. 4 is a sectional view taken along lines 4—4 of FIG. 2.

FIG. 5 is an enlarged view partially in section of the catheter at the point where it enters the penis.

FIG. 6 is a sectional view taken along lines 6—6 of FIG. 5.

FIG. 7 is an enlarged sectional view illustrating the proximal end of the catheter placed in the bladder during drug delivery procedures.

FIG. 8 is a sectional view taken along lines 8—8 of FIG. 7.

FIG. 9 is a perspective view cross sectioned and broken to show a second embodiment of the catheter which allows natural functioning of the patients spincter valves.

FIG. 10 is a sectional view taken along lines 10—10 of FIG. 9.

DESCRIPTION OF THE SPECIFIC EMBODIMENTS

Referring to the figures, there is shown a catheter for continuous controlled devivery of drugs. FIG. 1 through FIG. 8 show a first embodiment of the catheter generally designated as 10 formed of a suitable flexible material such as latex, silicone, or elastomeric polymers all of which are shown in the prior art. Catheter 10 has a distal end 12 which remains outside the body and a proximal end 14 which is placed in the bladder.

An inflatable retention balloon 16 is located near but spaced from the proximal end 14. While a balloon is preferred other prior art retention means may be utilized. Located between the retention balloon 16 and the end 14 are drainage openings 18 which connect to a central drainage lumen 20 which extends the full length of the catheter 10 terminating at the distal end 12 with a funnel structure 22 suitable for connection to a drainage tube attached to a urine collection bag. Distal to but in close proximity to the retention balloon 16 and at a location which would be adjacent to the prostate gland when the catheter is properly placed within the male urinary tract is a permeable membrane bag 24. The membrane bag surrounds the catheter 10 enclosing drug outlet 26 which is the terminus of the drug delivery lumen 28. Drug delivery lumen 28 terminates on its other end at side tube 30 which has a valve 32 at the distal end thereof through which the desired drug is injected or continuously fed. To facilitate dispersion of the drug being introduced to the space between the outer surface of the catheter enclosed within the membrane bag 24 a groove 34 is formed in the surface of the catheter 10. The space 27 may be partially or totally filled with an open pore sponge-like material 29 to facilitate dispersion of the fluid through the space 27. Connected to retention balloon 16 through inflation opening 36 is inflation lumen 38 which is accessed through inflation side arm 40 and inflation valve 42.

In order to retain the catheter 10 in its position in the penis, formed integrally with the the distal end of the catheter is a sheath 44 of a non-permeable material, preferably the same material from which catheter 10 is produced. The sheath 44 is placed over the penis in the same manner as a condom producing a leak proof covering over and around the end of the penis as shown in FIG. 2 and 5. To improve the leak proof nature of the sheath 44 a non-allergenic tissue compatible adhesive 46 may be applied to the skin contacting surface of the sheath 44.

Catheter 10, retention balloon 16, side tube 30 and inflation side arm 40 are fabricated in a manner similiar to prior art foley catheters from flexible rubbery materials such as latex, silicone rubber, polyurethane or thermoelastomeric materials into a single unitary structure. The membrane bag is then molded to, adhesively adhered or bonded to the surface of the catheter in a manner which would preclude leaking of liquid substances through the bonded connection. The membrane bag 24 is composed of a permeable material which is not water soluable such as permeable or semi-permeable membranes of cellulosic, acrylic (HEMA or like materials), polyurethane, polycarbonate, polyvinyl pyrrolidone, polyvinyl alcohol, or other materials known to be capable of controlled slow release of drugs from solutions. If desired the space between membrane 24 and the wall of catheter 10 can be partially or totally filled with a cellular sponge like material to aid in the distribution of the drug to be delivered. In addition, the whole device can be coated with a hydrophilic material which makes the catheter lubricious when wet to aid in insertion or suitable for the application of drugs such as antibiotics or antimicrobials to the catheter surface.

The device of the invention can be utilized for the delivery of antibacterial or antimicrobial materials to the urethra to counteract or prevent retrograde infection. However its preferred function is the slow, controlled long term delivery of drugs to the prostate gland to combat enlarged glands or the growth of cancerous tissue. One of the major problems of chemotherapy drugs used to treat tissue growth or tumors is that when delivered systemically to the body in dosages adequate to create the desired effect at the site of the cancer the drug has toxic effects on other bodily organs. Also the drug may be modified as it passes through the body such that its effect on the cancerous growth is not the same as if delivered directly. Often it is impossible to deliver an adequate dosage to the site of the tumor. For example anthracycline antibiotics (i.e., doxorubicin or Adriamycin) are cardiotoxic. Treatment for prostate cancer is generally directed to procedures which interfer or reduce the production of di-hydrotestosterone such as the delivery of diethylstilbestrol (DES). Recently, injectable luteinizing hormone-releasing (LHRH) agonists have been developed. LHRH depresses testosterone and di-hydrotestosterone production. Oral antiandrogen hormonal therapy has also been developed. However, since these drugs are delivered systemically they can have systemic side effects. The preferred route would be to deliver effective drugs continuously and at high doses directly to the tumor. Drugs which have been shown to be effective in treating prostate carcinoma include 2,6-cisdiphenylhexamethylcyclotetrasiloxane, chymotrypsin, 3,5-bis(substitited amino)-1,2,4-dithiazolium salts, 3 substituted amino- 5 substituted imino-1,2,4-dithiazoline salts and dithiobiuret intermediates, 4-(4H-benzo(4,5)cyclohepta (1,2-B)thiophen-4-ylidene)-1-methylpiperidines, 1-docsanol, 13-cis-docsen-1-ol, 9-cis,12-cis-octadecadien-1-ol, 2-eicosnaol, 5,10-secosteroids, derivatives of 1,2-diphenyl-ethane, derivatives of 17-alpha-hydroxy,19-nopregn-4-ene-3,20-dione, 17-beta-ethynyl-3,17-alpha-estradiol and derivatives thereof, nonapeptide amides, fungimycin compositions, MK-906 (Merck, Sharpe and Dome), fluorocil, ketoconosol and hemostatic agents. However, the invention also contemplates the direct delivery of yet to be discovered drugs as well as drugs only effective for treating the prostate when delivered directly as they are to toxic or short lived for systemic delivery by the oral or injection route.

To utilize the invention the catheter 10 is inserted through the urethra using generally practiced procedures for placing urinary drainage catheters. Once the proximal end 14 of the catheter and the uninflated retention balloon are within the urinary bladder the balloon is inflated by introducing a specified amount of air, sterile water or saline solution through inflation valve 42 located on the end of inflation side arm 40 and inflation lumen 38. Catheter 10 is then tugged so that the inflated retention balloon 16 is snug against the neck of the urinary bladder. The sheath 44 is then rolled back over the outer surface of the penis forming a liquid tight enclosure around the meatus of the penis. To treat the prostate a solution of the desired drug is prepared and the desired quantity is placed into a syringe. Valve 32 is punctured by the syringe and the medication is introduced through the drug delivery lumen 28 into the space between the catheter wall and the membrane bag 24 inflating the membrane bag 24. Due to the porous nature of the membrane material the medication passes through the membrane and directly impinges against and infuses into the prostatic ducts. The rate of delivery of the drug can be controlled by varying the pressure under which the drug is introduced, the concentration of the drug in its carrier, and the porosity of the membrane. Alternatively, a continuous delivery pump can be connected to the drug side tube 30 so that the delivery rate is controlled by the pump settings.

FIGS. 9 and 10 Show an alternative embodiment of the catheter 10. Like features are represented by the same numbers as in FIGS. 1-8. This embodiment incorporates features which would allow the urinary spincters at the neck of the bladder and along the urethra to perform their normal function. Between the retention balloon 16 and the membrane bag 24 the catheter wall has a soft section 48 which allows the urinary spincter to compress the catheter occluding the drainage lumen. Also the proximal end of the catheter consists only of the inflation side arm 40 and the drug side tube 30 which are shaped as half circles (see FIG. 10). The spincter within the urethra holds these two tubes in contact thus occluding the proximal end of the drainage lumen. Relaxation of the spinter muscles to allow voiding of the bladder allows the resiliant material of the catheter to open the lumen in the area of the soft section 48 and the flat walls 52 and 54 of the drug and inflation tubes 30 and 40 separate thus facilitating voiding in a normal manner, thus avoiding the need for a urinary drainage bag.

While the devices described are for the delivery of drugs to the prostate the invention contemplates the use of similar tubular devices properly sized and shaped for delivery of drugs to other hollow body organs.

What is claimed is:

1. A system for the controlled, continuous delivery over an extended period of time of a drug containing fluid to the prostate comprising a catheter including an elongated tubular member having an external distal end and a proximal end for placement into the urinary bladder through the male urethra, expandable means adjacent the proximal end to retain the catheter in sealing abutment against the neck of the bladder, an expandable porous membrane bag integral with and spaced from the outer surface of said tubular member, distal to the expandable means for retention of the catheter, a drug lumen within said tubular wall connecting the space between the outer surface of said tubular member and the membrane bag with a valve mounted on the distal end of the lumen for the introduction of the drug to the prostate, said membrane positioned so that upon placement of the catheter the membrane bag is adjacent the prostate ducts, the catheter having a lumen within the wall of said tubular member connecting the expandable retention means with a valve on the distal end of said tubular member the elongated tubular member also having a drainage lumen therein extending from the proximal end only partially along the length of the elongated member, the expansion lumen and the drug lumen for a portion of their length being enclosed within tubular members having semicircular crosssections and opposing flat surfaces.

2. The catheter of claim 1 further having a sheath integral with said tubular member distal end, said sheath being condom shaped for leakproof covering of at least the meatus of the penis when the catheter is positioned in the urethra.

3. The catheter of claim 2 wherein said means for retention is an inflatable balloon.

4. The catheter of claim 1 further having the space between the porous membrane and the tubular member at least partially filled by an open pore compressible sponge like material.

* * * * *